(12) United States Patent
Kim et al.

(10) Patent No.: US 9,001,323 B2
(45) Date of Patent: Apr. 7, 2015

(54) METHOD OF FABRICATING GOLD NANOSTRUCTURES USING ELECTROLESS DISPLACEMENT PLATING

(75) Inventors: Sang Kyung Kim, Seoul (KR); Sang Hwi Park, Jinju-si (KR)

(73) Assignee: Korea Institute of Science and Technology, Seoul (KR)

( * ) Notice: Subject to any disclaimer, the term of this patent is extended or adjusted under 35 U.S.C. 154(b) by 281 days.

(21) Appl. No.: 13/608,651

(22) Filed: Sep. 10, 2012

(65) Prior Publication Data
US 2013/0094021 A1    Apr. 18, 2013

(30) Foreign Application Priority Data

Oct. 18, 2011 (KR) .......................... 10-2011-0106589

(51) Int. Cl.

| | |
|---|---|
| G01J 3/44 | (2006.01) |
| C22C 5/02 | (2006.01) |
| G01N 21/65 | (2006.01) |
| C23C 18/54 | (2006.01) |
| B82Y 30/00 | (2011.01) |
| B22F 1/00 | (2006.01) |
| B82Y 40/00 | (2011.01) |

(52) U.S. Cl.
CPC .............. *C22C 5/02* (2013.01); *G01N 21/658* (2013.01); *C23C 18/54* (2013.01); *B82Y 30/00* (2013.01); *B22F 1/0018* (2013.01); *B22F 1/0062* (2013.01); *B82Y 40/00* (2013.01); *B22F 2001/0037* (2013.01); *B22F 2999/00* (2013.01)

(58) Field of Classification Search
USPC ............................................. 356/301, 72–73
See application file for complete search history.

(56) References Cited

U.S. PATENT DOCUMENTS 7,400,395 B2 *    7/2008   Chan et al. ................... 356/244

FOREIGN PATENT DOCUMENTS

| KR | 10-2009-0126825 | 12/2009 |
| KR | 10-2011-0003076 | 1/2011 |

OTHER PUBLICATIONS

W.A. El-Said et al., "Detection of effect of chemotherapeutic; agents to cancer cells on gold nanoflower patterned substrate using surface-enhanced Raman scattering and cyclic voltammetry", Biosensors and Bioelectronics, 2010, 7 pages.
Yongxia Huang et al., "SERS study of Ag nanoparticles electrodeposited on patterned $TiO_2$ nanotube films", Journal of Raman Spectrosopy, 2011, 42, pp. 986-991.
S. L. Smitha et al., "Gold nanorods with finely tunable longitudinal surface Plasmon resonance as SERS substrates", Nanotechnology 22, 2011: 265705, pages 7.

* cited by examiner

*Primary Examiner* — Abdullahi Nur
(74) *Attorney, Agent, or Firm* — Goldilocks ZONE IP LAW

(57) ABSTRACT

The present invention provides a method of fabricating gold nanoparticles using electroless displacement plating, the method including the steps of: depositing on a substrate a metal having a reduction potential lower than that of gold to form a metal layer; and reacting a gold ion-containing plating solution with the metal layer. The invention also provides gold nanoparticles fabricated by the method. According to the method, gold nanostructures can be fabricated in a simple, cost-effective and efficient manner, and the fabricated gold nanoparticles can be used to measure surface-enhanced Raman scattering (SERS) signal or fluorescence. In addition, the invention enables the development of an optical sensor including the gold nanostructures.

11 Claims, 12 Drawing Sheets

METHOD OF FABRICATING GOLD NANOSTRUCTURES USING ELECTROLESS DISPLACEMENT PLATING

CROSS-REFERENCE TO RELATED APPLICATION

This application claims priority under 35 U.S.C. §119 to Korean Patent Applications No. 10-2011-0106589, filed on Oct. 18, 2011 in the Korean Intellectual Property Office, the disclosure of which is incorporated herein by reference in its entirety.

BACKGROUND OF THE INVENTION

1. Field of the Invention

The present invention relates to a method of fabricating gold nanostructures using electroless displacement plating, and gold nanostructures fabricated thereby.

2. Description of the Prior Art

Conventional methods for fabricating nanostructures include electron beam lithography, nano-imprint lithography, focused ion beam lithography, electrochemical deposition, etc.

Electron beam lithography is a process of fabricating nano-sized patterns using electronic energy, in which an electron beam emitted from an electron gun is focused with an electromagnetic lens and is precisely deflected and scanned, thereby processing a resist. In the subsequent process, the resist is developed and the substrate is wet or dry etched, like a general semiconductor process. This method enables the fabrication of patterns having a size of a few nm, but has a disadvantage in that, because focused nano-sized beams are scanned one at a time, too much time is required to pattern a large area, making mass production difficult.

Nano-imprint lithography is a process of patterning a polymer resin by UV or heat, in which a stamp having a pattern protruding from the surface thereof is required for patterning. In order to fabricate the stamp, electron beam lithography and dry etching are generally used. The nano-imprint lithography process enables the fabrication of patterns having a size of several tens of nm, but has disadvantages in that patterns are distorted due to thermal expansion resulting from the difference in material between the stamp and the substrate and in that the application of high pressure is required.

Electrochemical deposition is a process of forming a metal coating layer using electrical energy. It uses an electrochemical reaction. Specifically, when the metal (steel plate) to be plated is negatively charged and placed in a plating solution and an electric current is applied thereto, a metal ion in the plating solution moves to the negative electrode. This process is easily performed, but has a disadvantage in that it is difficult to form a gap at a desired position.

Plating processes are broadly classified into two: electroplating in which the rate of plating is controlled in proportion to the intensity of voltage; and electroless plating the rate of plating is controlled according to the difference in reduction potential from a seed metal and to reaction conditions.

Electroless plating refers to forming a coating layer of a desired metal on the surface of interest by applying an electric current to an electrolyte solution containing a metal ion. Electroplating is a process which is applied to various products, including electronic parts, fancy goods, industrial products, etc. The electroplating is advantageous in that the reaction rate is high, but is disadvantageous in that it is difficult to fabricate nanostructures uniformly on a large area.

Meanwhile, previous studies on the fabrication of gold nanostructures include a method of fabricating gold nanostructures by applying external voltage (Biosensors and bioelectronics 26 (2010) Detection of effect of chemotherapeutic agents to cancer cells on gold nanoflower patterned substrate using surface-enhanced Raman scattering and cyclic votammerty) (J. Raman Spectrosc. 2011, 42, pp. 986-991, SERS study of Ag nanoparticles elelctrodeposited on patterned $TiO_2$ nanotube films), and a method of fabricating gold nanostructures using other media, including a micelle templates and surfactants (Nanotechnology, 22 (2011) 265705, Gold nanorods with finely runable longitudinal surface plasmon resonance as SERS substrates).

PRIOR ART DOCUMENTS

Non-Patent Documents

Biosensors and bioelectronics 26 (2010) Detection of effect of chemotherapeutic agents to cancer cells on gold nanoflower patterned substrate using surface-enhanced Raman scattering and cyclic votammerty.

J. Raman Spectrosc. 2011, 42, pp. 986-991, SERS study of Ag nanoparticles elelctrodeposited on patterned $TiO_2$ nanotube films.

Nanotechnology, 22 (2011) 265705, Gold nanorods with finely runable longitudinal surface plasmon resonance as SERS substrates).

SUMMARY OF THE INVENTION

Accordingly, the present invention has been made in view of the problems occurring in the prior art, and it is an object of the present invention to provide a method of fabricating gold nanostructures uniformly on a large area in an easy and simple manner without using other media, applying voltage and using electrical energy.

One embodiment of the present invention provides a method of fabricating gold nanoparticles using electroless displacement plating, the method including the steps of: depositing on a substrate a metal having a reduction potential lower than that of gold to form a metal layer; and reacting a gold ion-containing plating solution with the metal layer.

One embodiment of the present invention provides a method of measuring surface-enhanced Raman scattering (SERS) signal or fluorescence using gold nanostructures fabricated by the above method.

One embodiment of the present invention provides gold nanostructures fabricated by the above fabrication method.

One embodiment of the present invention provides gold nanostructures including nanostructures formed by plating gold on a substrate, in which the nanostructures are nanoflowers or nanolawns.

One embodiment of the present invention provides an optical sensor including gold nanostructures fabricated by the above fabrication method.

BRIEF DESCRIPTION OF THE DRAWINGS

The above and other objects, features and advantages of the present invention will be more clearly understood from the following detailed description taken in conjunction with the accompanying drawing, in which.

DETAILED DESCRIPTION OF THE INVENTION

Figure 1:
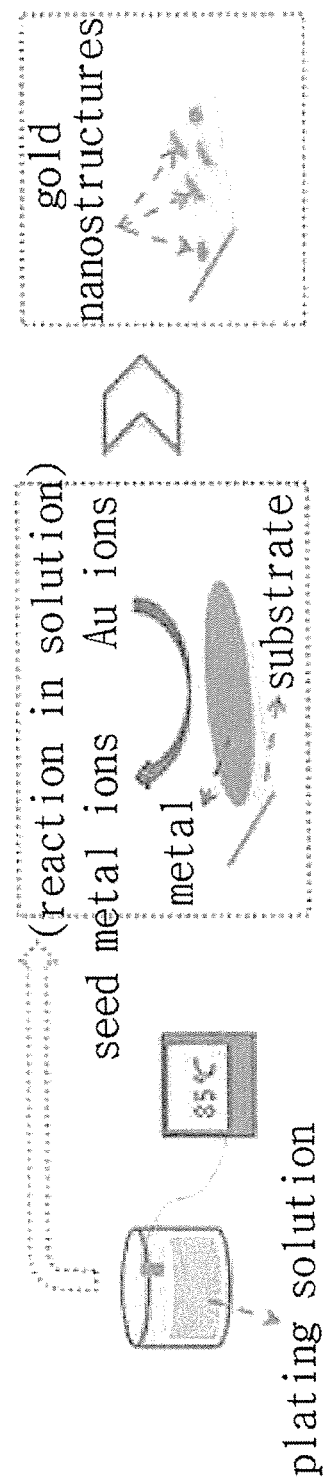
FIG. 1 shows a process of fabricating gold nanostructures.
Figure 2:
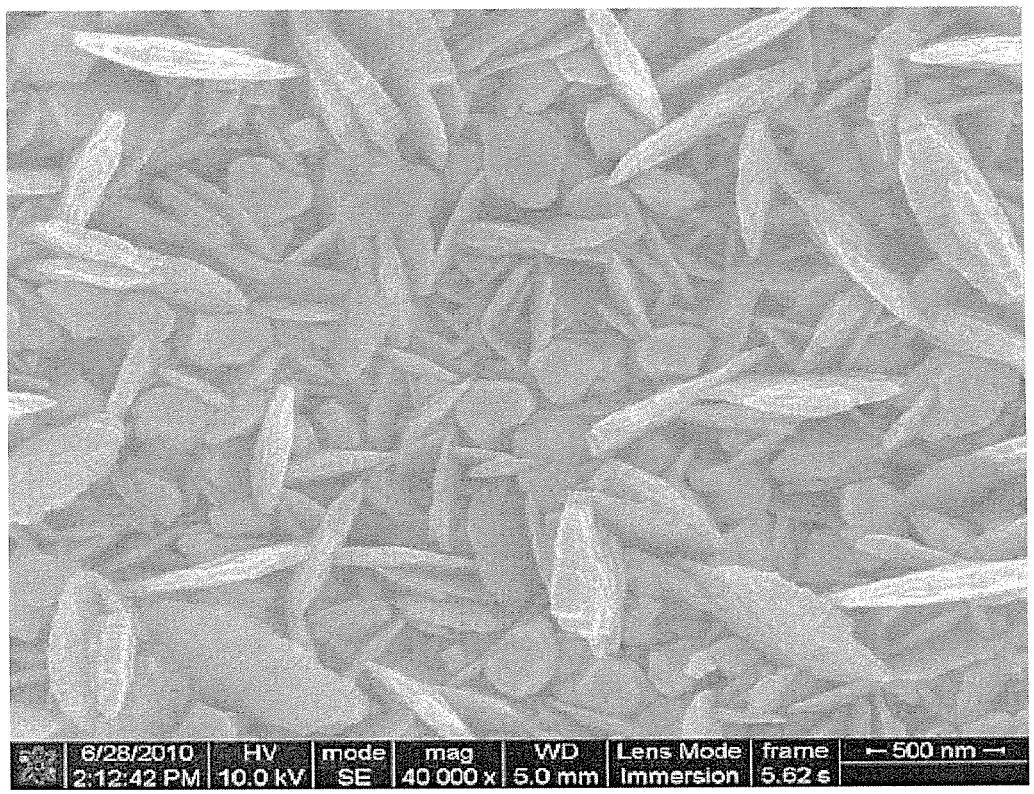
FIG. 2 shows an SEM image of fabricated gold nanostructures.

Hereinafter, the present invention will be described in detail.

The present invention provides a method of fabricating gold nanoparticles using electroless displacement plating, the method including the steps of: depositing on a substrate a metal having a reduction potential lower than that of gold to form a metal layer; and allowing a gold ion-containing plating solution to react with the metal layer.

As used herein, the term "electroless displacement plating" refers to a plating process in which, when the surface to be plated is brought into contact with a solution containing a metal salt and a reducing agent, an electron resulting from the oxidation of a seed metal is transferred to a gold ion present in the solution to form a metal coating layer. This plating process has advantages in that it is advantageous for forming a uniform thickness and is simple. Electroless plating processes are broadly classified into three: an autocatalytic process; a substrate catalytic reaction process; and a galvanic displacement process.

The autocatalytic process is a plating process which is most frequently used in the electronic industrial field. In this process, plating is performed by depositing a metal by adjusting temperature and pH using a metal salt, a reducing agent and an additive without applying external electric power, in which the metal is produced by chemical reduction. This chemical reduction is an autocatalytic reaction which occurs on the catalyst surface so as to allow plating to continue.

The substrate catalytic reaction process is similar to the autocatalytic process, but differs in that the reduction reaction occurs on the substrate surface.

The galvanic displacement process is a plating process in which a metal ions to be displaced in a potassium cyanide solution displaces a seed metal atom on the surface of a substrate metal by a strong redox displacement reaction with the seed metal atom. When the surface of the substrate metal is completely displaced by the displacement metal, the plating reaction is completed.

In the electroless displacement plating, the plating rate is high at an initial stage, but gradually decreases when a specific thickness or higher is reached. For example, when the thickness of plating reaches several hundreds of nm for silver (Ag) and several nm for copper, the plating rate gradually decreases. The present inventors have developed an optimal method of fabricating optimal nanostructures in plating of gold.

From a viewpoint of equilibrium electrochemistry, an electrochemical reaction spontaneously occurs when the Gibbs's free energy (i.e., free energy value) is negative. Based on this, the free energy value in the oxidation/reduction reaction is expressed as the difference in electromotive force between two electrodes.

$$\Delta G^0 = -nF\epsilon^0$$

For a spontaneous oxidation/reduction reaction, the free energy value should be negative, and thus the value of standard electromotive force ($e^0$) should be positive. The value of standard electromotive force ($e^0$) can be calculated using the standard electrode potential table and can be expressed as the following equation:

$$\epsilon^0 = E_r^0 - E_l^0$$

Particularly, in the galvanic displacement plating process, a reaction occurs when the Gibbs's free energy in the above two equations is negative and the electromotive force is positive. From the above equation of standard electromotive force ($e^0$), the value of standard electromotive force for two metals can be determined.

For example,

$$Ni \rightarrow Ni^2{.} + 2e$$

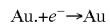
$$Au{.} + e^- \rightarrow Au$$

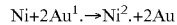
$$Ni + 2Au^1{.} \rightarrow Ni^2{.} + 2Au$$

In the above example, the standard electromotive force ($e^0$) for the two metals is positive, indicating that the Gibbs's free energy is negative. Thus, in the overall plating reaction, a nickel (Ni) ion is detached from a substrate, and an Au ion binds to a free electron and is deposited as Au.

The present invention provides a method of fabricating gold nanostructures using a modified galvanic displacement method. In the present invention, a seed metal has a reduction potential lower than that of gold. The order of ionization tendency of metals is as follows: K>Ca>Na>Mg>Zn>Cr>Fe>Co>Ni>Cu, Hg>Ag>Pd>Pt>Au. As it approaches the left side of the order of ionization tendency, the reduction potential tends to decrease (that is, the oxidation tendency increases). On the other hand, as it approaches the right side, the reduction potential tends to increase (that is, the reduction tendency increases). When gold (Au) among the metals is used as a replacement metal, Ni, Pt, Ag or Cu may be used as a seed metal having a reduction potential lower than that of gold. Preferably, Pt, Ag or Cu may be used. The metal layer may be deposited on the substrate to a thickness of 10-1000 nm. Table 1 below shows the standard electrode potentials of metals in an aqueous solution at 25° C.

TABLE 1

| Reaction | Potential(V) |
|---|---|
| $Pt^{2+} + 2e \rightarrow Pt$ | +1.118 |
| $Ag^{1+} + e \rightarrow Ag$ | +0.7991 |
| $Cu^{2+} + 2e \rightarrow Cu$ | +0.340 |
| $Ni^{2+} + 2e \rightarrow Ni$ | −0.257 |
| $Au^{1+} + e \rightarrow Au$ | +1.83 |

The growth mechanism of gold nanostructures can vary depending on a metal substrate. When electroless plating conditions were maintained constant for all four substrates (Pt, Ag, Cu and Ni), the resulting structures were quite unique for the metal substrates. This morphological difference is due to the standard electrode potential of each substrate. Among the metals, Ni is more electronegative (−0.257 V) than any other metals with respect to Au which is the most electropositive metal (1.83 V). In the case of the Ni substrate, Au ions are rapidly released, and the weaker interaction between the Au ions and other additives occurs, so that the formation of spheres can be induced, similar to the case with no additive. The standard electrode potential of Cu is +0.340 V which is far less electropositive than Au. Thus, the release rate of Au ions decreases and the interaction between Au ions and other additives is enhanced.

The formation of various shapes is likely the outcome of the interplay between the faceting tendency of a stabilizing agent present in an Au plating solution and the growth kinetics (rate of supply of $Au^0$ to the crystallographic planes). Although Ag is less electropositive (+0.799 V) than Au, it can be partially replaced. In electroless metal plating, reduced Ag ions act as sacrificial seeds for the reduction of $Au^{3+}$ ions to form Au tubes or rods.

Figure 3:
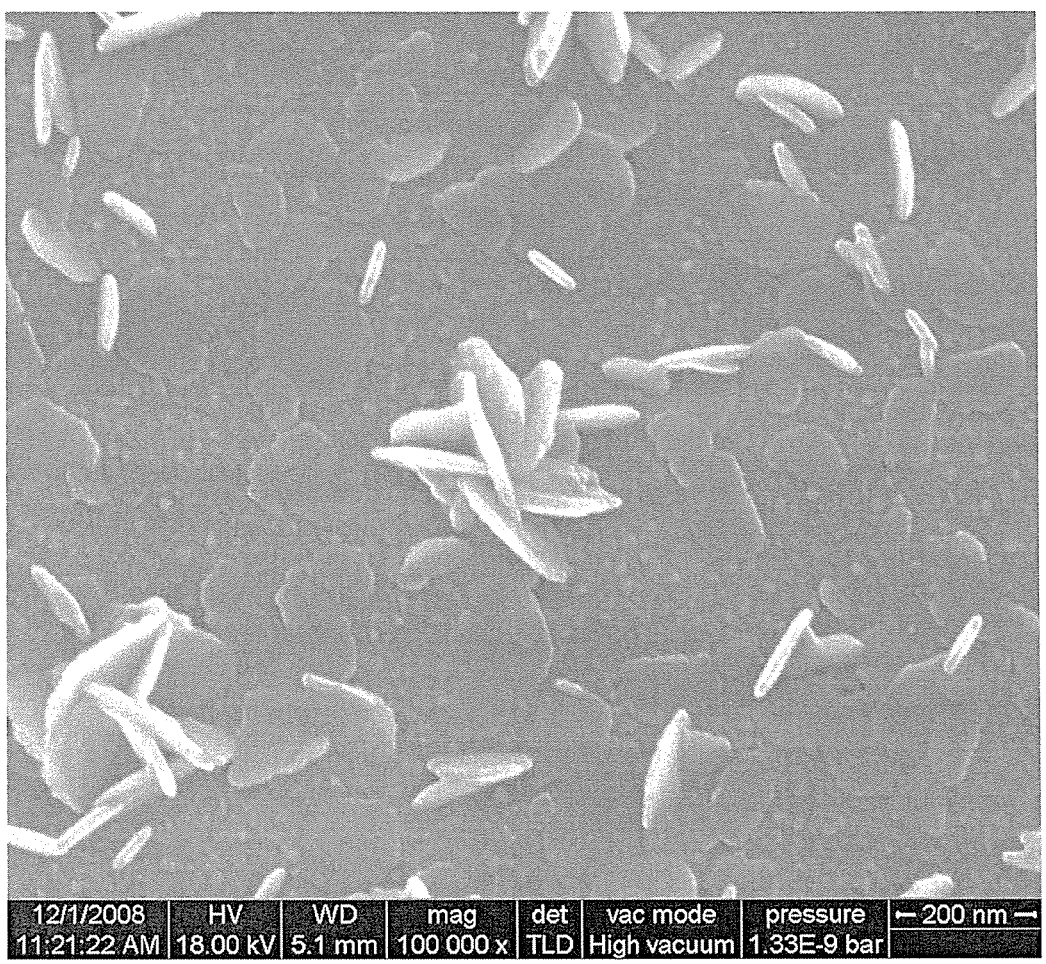
FIG. 3 shows nanostructures formed by replacing Pt as a seed metal by Au.
Figure 4:
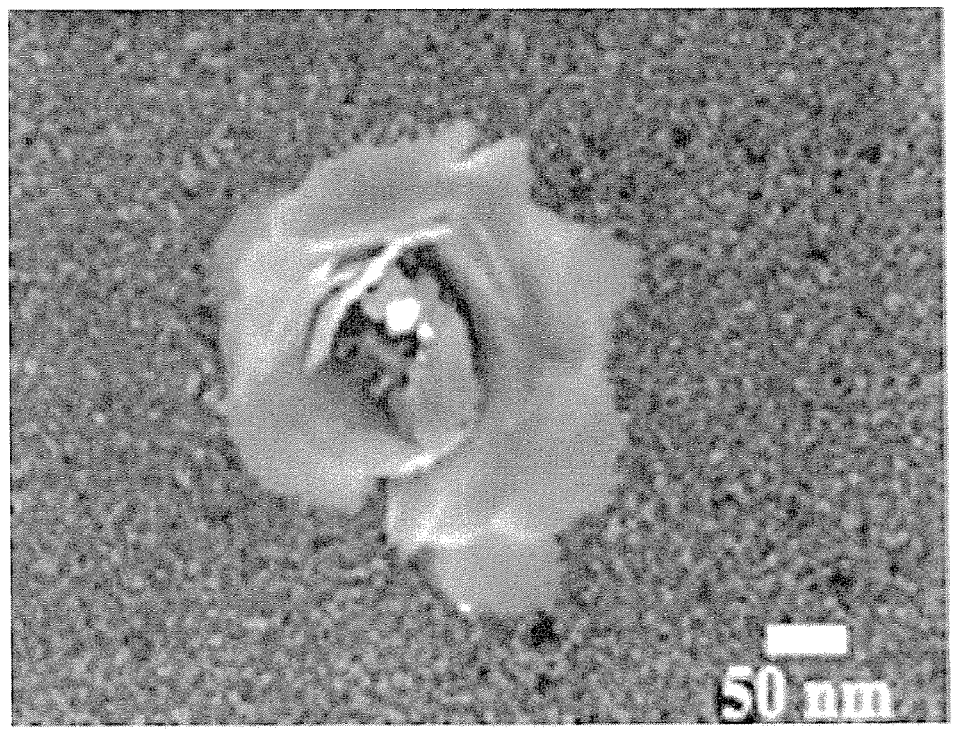
FIG. 4 shows nanostructures formed by replacing Ag as a seed metal by Au.
Figure 5:
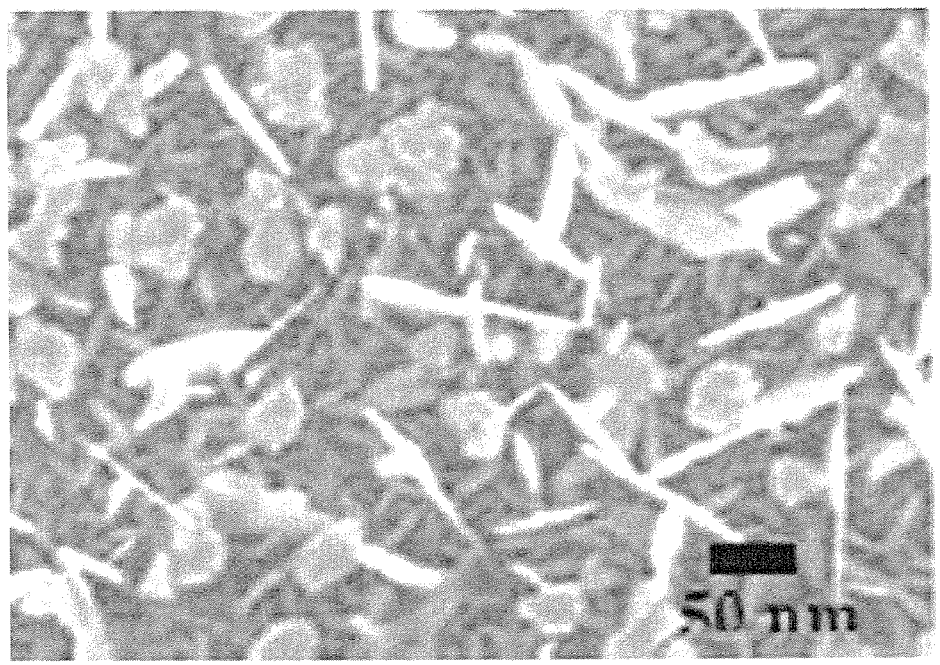
FIG. 5 shows nanostructures formed by replacing Cu as a seed metal by Au.

In the present invention, the gold nanostructures may be nanoflowers or nanolawns. As can be seen in FIG. 3, when platinum as a seed metal is replaced by gold, nanolawns can be formed. Moreover, as can be seen in FIG. 4, when Ag as a seed metal is replaced by gold, nanoflowers can be formed. In addition, as can be seen in FIG. 5, when Cu as a seed metal is replaced by gold, nanolawns can be formed.

The fabrication method of the present invention may further comprise, before the step of forming the metal layer, a step of depositing Ti on the substrate. The deposition of Ti is carried out in order to increase the adhesion between the substrate and the metal layer. Ti is deposited on the substrate to a thickness of 1-50 nm, preferably 5-20 nm, and then the seed metal layer is preferably deposited on the Ti layer.

The fabrication method of the present invention may further comprise, after the reaction step, a step of cooling the plating solution for 2-5 minutes to grow the gold nanostructures on the metal layer. When gold is plated on metals having reduction potentials higher than that of Ni, it is preferred to carry out cooling at room temperature for 2-5 minutes after the plating reaction. Herein, the room temperature is preferably about 10~30° C. During the cooling process, nanoflower or nanolawn structures can be formed.

In the present invention, the reaction step is carried out at a temperature of 80~90° C., and preferably 83~87° C. If the reaction step is carried out at a temperature lower than 80° C., little or no reaction will occur and partially spherical structures will be formed, and if the reaction step is carried out at a temperature higher than 90° C., a complete replacement with gold will occur, but partially spherical structures will be formed in large amounts. For this reason, in order to gold nanostructures, including nanoflower or nanolawn structures, the reaction step is carried out at a temperature of 80~90° C., and preferably 83~87° C.

During the reaction, the reaction temperature is decreased by 1~5° C., and preferably 1~2° C., compared to the initiation temperature of the reaction. If the reaction temperature is maintained constant, the reaction will occur faster, and spherical structures will be formed, but if the reaction is carried out while the initiation temperature of the reaction is decreased, nanoflower or nanolawn structures will be formed.

In the present invention, the reaction step may be carried out for 2 minutes or more. In the inventive method of fabricating gold nanostructures using electroless displacement plating, it can be seen that, when the reaction step is carried out for 2 minutes or more, nanoflower or nanolawn structures can be formed. When a test was carried out at 80° C., it could be seen that, when the reaction was carried out for 2 minutes, nanolawn structures were formed, and then spherical structures were formed with the passage of time, and after 24 hours, formed into larger nanolawn structures. When a test was carried out at the optimum temperature of 83~85° C., it could be seen that structures corresponding to the structures obtained after 24 hours were formed immediately after 2 minutes.

In the present invention, the reaction step may be carried out at a rate of 10-100 rpm. When the rate of the reaction between the gold ion-containing plating solution and the metal layer was higher than 100 rpm, it could be seen that some nanoflower or nanolawn structures were formed, the size thereof was relatively small, and partially spherical structures appeared. When the reaction was carried out at a relatively low rate, it could be seen that nanoflower or nanolawn structures having small size were formed. If the rate of the reaction is lower than 10 rpm, the reaction cannot easily occur. In addition, the difference in reduction potential between Au and other substrate influences the growth rate of gold nanostructures. The difference in standard electrode potential between Pt (+1.188 V) and Au (+1.83 V) is far less than any of the above metals. Interestingly, small grain-like structures are formed on the surface, and then as the reaction proceeds for several hours, this grain enlarges like a pod and further results in a branched multipod. In the case of the Au substrate, the formation of some stable complexes can reduce the production rate of Au ions in a solution. The relatively low production rate of Au ions is favorable for the continuous growth of 3D hierarchical nanostructures. The gold nanostructures grown on Pt and Ag show a highly selective and anisotropic geometry. The replacement with Au is in the order of Ni>Cu>Pt>Ag. This is because the retarded reaction rate stabilizes a complex of $Au^{3+}$ ions and additives to enable the selective growth of Au.

In the reaction step of the method of the present invention, the reaction of the deposited metal layer with the plating solution can be carried out before the oxidation of the metal occurs. In other words, the surface of the deposited metal layer oxidizes with the passage of time after the deposition, and for this reason, the deposited metal layer preferably reacted with the plating solution immediately before it oxidizes.

The present invention provides gold nanostructures fabricated by the above fabrication method.

The present invention also provides gold nanostructures formed on a substrate, in which the nanostructures are nanoflower or nanolawn structures.

The present invention also provides an optical sensor comprising gold nanostructures fabricated by the above fabrication method. The optical sensor may comprise a fluorescent molecule having a quantum yield of less than 50%, for example, Cy3. When fluorescence is measured using Cy3, the effect of fluorescence amplification can be significantly increased. Thus, the use of Cy3 enables the development of an optical sensor.

According to the present invention, surface-enhanced Raman scattering (SERS) signal can be measured using the gold nanostructures fabricated by the above fabrication method. The gold nanostructures fabricated by the method of the present invention have advantages in that they generate a strong SERS signal and are highly biocompatible, suggesting that they can be applied to biosensors.

In addition, according to the present invention, fluorescence can be measured using the gold nanostructures fabricated by the above fabrication method.

The fabrication method of the present invention may comprise a step of coating the fabricated gold nanostructures with a positively charged polymer. The positively charged polymer may be selected from the group consisting of polyethylene imine or its derivatives, polylysine, chitosan, poly-aspartic acid, spermine, protamine, polyamidoamine, polypropyleneimine, polybrene, polyacrylamide, polyvinyl amine, and DEAE-dextran. It can be seen that, when the gold nanostructures are coated with the positively charged polymer, the effect of fluorescence amplification can be increased.

Furthermore, the measurement of fluorescence can be performed using a fluorescent molecule having a quantum yield of less than 50%, for example, Cy3. It could be seen that, when fluorescence was measured using Cy3, the effect of fluorescence amplification was significantly high. It could be seen that, in the case of Cy3 having a quantum yield of 10%, the effect of fluorescence amplification increased 5-10 times. Table 2 below shows the ratio of amplified fluorescence intensities as a function of the molecular weight of chitosan and the kind of fluorescent molecule when gold nanostructures are coated with chitosan.

TABLE 2

| Molecular weight of chitosan | Cy3 staining (quantum yield: 10%) | FAM staining (quantum yield: 90%) |
| --- | --- | --- |
| 1000 | Inano/Ibare: 15 | Inano/Ibare: 3.69 |
| 5000 | Inano/Ibare: 3.0 | Inano/Ibare: 3.05 |

Before coating with chitosan, the fluorescence signal from the nanostructure substrate increased about 1.5 times, and after coating with chitosan, the fluorescence signal from the nanostructure substrate increased about 3 times. However, among the nanostructures coated with the chitosan having a molecular weight of 1,000, the fluorescence measured on the nanostructure substrate using the Cy3 fluorescent molecule increased 5-10 times. This result suggests that a surface for use as an optical sensor is advantageously a surface which has gold nanostructures and uses the Cy3 fluorescent molecule.

Hereinafter, the present invention will be described in detail with reference to examples. It is to be understood, however, that these examples are for illustrative purposes only and are not intended to limit the scope of the present invention.

Example 1

Preparation of Reagents

To an LECTLESS FX-5 basic solution (manufactured by Enthone Inc.), 2 g/l of Au was added to prepare an Au metal salt solution which was then adjusted to a pH of 4.7 using a pH Basic-A solution. 4-Aminobenzenethiol having a purity of 97% was purchased from Sigma Aldrich, USA. Absolute ethanol of analytical grade used as a solvent to dissolve 4-ABT was purchased from Carlo Erba reagents, Italy.

Example 2

Synthesis of Gold Nanoflowers and Nanostructures

FIG. 1 schematically shows a process of fabricating gold nanostructures. Crystalline (100) p-type Si wafers were cleaned using the standard RCA method, and then Ti was deposited on each Si surface to a thickness of 100 Å. Then, each of Ni, Pt, Ag and Cu was deposited on each sample to a thickness of 1000 Å. Herein, both the Ti layer (100 Å) and the metal layer (1000 Å) were deposited using an e-beam evaporator (Ultech) at a rate of 3 Å/s. The evaporation base pressure was $2 \times 10^{-6}$ Torr. After deposition of the metal, the substrate was immersed in a electroless plating solution containing a dilute Au metal salt [$KAu(CN)_{2aqua}$]. This Au metal salt present in this solution replaced the metal layer by an Au metal layer. The temperature of the solution was maintained at 80° C. using a double boiler. The replacement was carried out for 2 min. The solution was stirred with a magnetic stirrer. After 2 min of the reaction, the replaced gold grains were distributed as seeds on the metal substrate. The substrate immersed in the Au plating solution remained undisturbed. The reactor containing the Au plating solution was removed from the hot plate. The Au plating solution containing the substrate was cooled at room temperature. As a result, the growth of nanoflowers occurred on the metal layers made of Ag, Cu and Pt, respectively, at room temperature. The reaction process was carried out for each of 2 min, 12 hr, 18 hr, 24 hr and 48 hr.

The test conditions were maintained constant for all the three substrates (Ni, Pt and Ag). The as-synthesized products were observed using SEM. Each of thin Pt films was allowed to react with a plating solution. Au nanostructures on the Pt substrates were generated for 12 hr, 24 hr or 48 hr. FIG. 3 shows the surface morphology of the Au nanostructures formed on the Pt substrate. The SEM image of FIG. 3 shows flower-like structures, and thus the nanostructures were named nanoflowers. Larger protrusions (petals) on the sample which was allowed to react for 24 hr had a length of 150-900 nm, a width of 00-300 nm and a thickness of 20-100 nm. Smaller protrusions (pods) had a length of 800-1200 nm, a width of 150-300 nm and a thickness of 30-100 nm. Branch structures grown out from the main petals were observed. Similar nanostructures were grown on an Ag substrate for 48 hr. FIG. 4 shows the nanoflower structures. Nanostructures formed on the Cu substrate appeared like nanolawns and did not appear flowers. FIG. 5 shows the nanolawn structures. The nanostructures grew faster on the Cu substrate. The shape of the nanostructures can vary depending on the choice of the metal substrate. From XPS analysis, it was demonstrated that the Pt metal was replaced by Au and that the increase in reaction time led to an increase in the content of Au.

Figure 6:
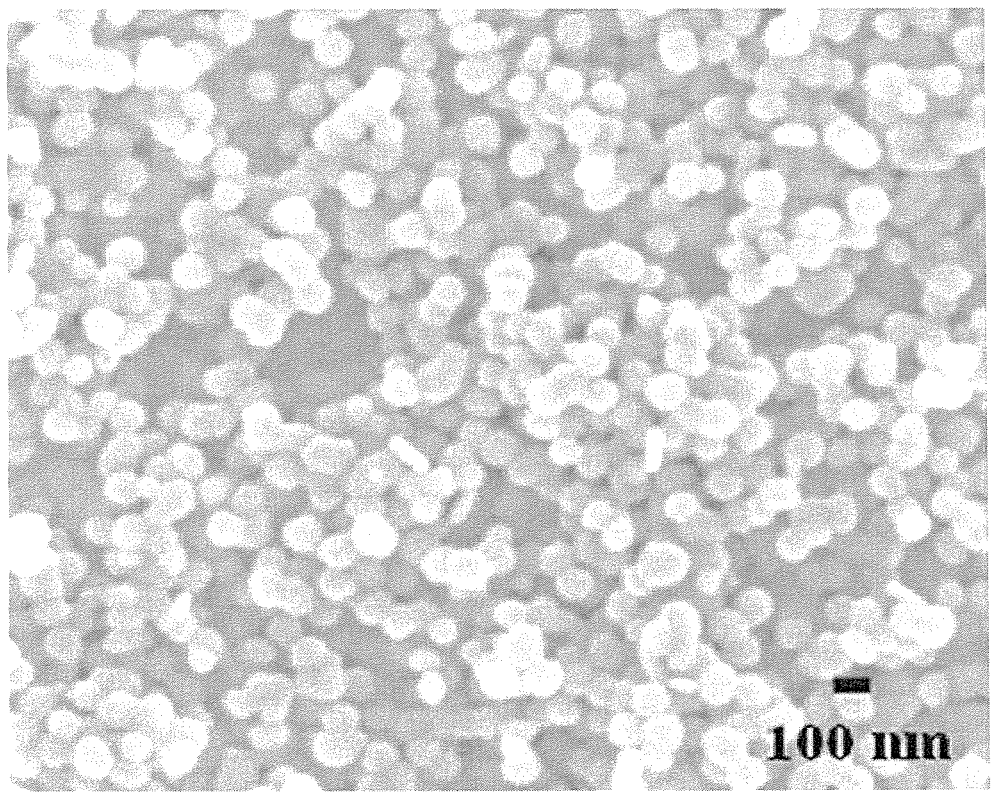
FIG. 6 shows nanostructures formed by replacing Ni as a seed metal by Au.

Ni was used as a reference for all other substrates. The Ni layer having a thickness of 1000 Å was deposited on the Ti layer having a thickness of 100 Å. The Au electroless plating on the Ni layer was carried out for 2 min to completely replace the Ni with an Au layer. The Au layer that replaced the Ni atoms as seeds showed spherical Au particles rather than any nanostructures. FIG. 6 shows the spherical structures. Selected area electron diffraction (SAED) shows that the nanoflowers were crystalline and randomly oriented. In addition, the electron diffraction pattern could be indexed as the face centered cubic (f cc) structure of Au.

Example 3

Characterization of Nanostructures and Measurement of SERS Signal

The nanostructures formed in Example 2 were characterized using scanning electron microscopy (SEM, FEI NOVA NanoSEM 200, kV) and high-resolution TEM (HRTEM, FEI Tecnai F20, 200 kV) by the Korea Institute of Science and Technology (KIST). Fast Fourier transform (FFT) measurements were carried out using a HR-TEM system. The nanostructures were characterized using focused ion beam microscopy (FIB, FEI NOVA 600 Nanolab, 30 kV) by the Korea Advanced Nano Fab Center (KANC). For the TEM measurements, the gold product was suspended in water by ultrasonication, and the suspension was dropped onto a Formvar-covered copper grid and naturally dried in the air. In order to verify the Au nanostructures for surface-enhanced Raman scattering (SERS), 4-ABT was assembled onto the substrate which had been soaked in 1 mM ethanol solution overnight. The instrument employed was an inverted confocal microscope. The linearly polarized excitation light from a HeNe laser (633 nm) was delivered into the entrance port of the inverted confocal microscope through a 50:50 beam splitter, and was focused on the sample surface by an objective lens 1.4 NA. The back-scattered Rayleigh radiation was transmitted by a Raman edge-filter in front of a spectrograph system (a monochromator and a TE-coated CCD camera). The SERS images were acquired simultaneously by raster-scanning the sample using a closed loop piezo-scanner. The SERS signal used for image formation was obtained by integrating over a $v_1$-Raman band and correcting for the thermal baseline of the CCD camera signal. The typical exposure time for each pixel in the image was 20 ms.

FIGS. 3 to 6 show SEM photographs of the gold nanostructures formed on each of the substrates. HR-TEM images of the Au nanostructures formed on the Pt, Ag and Cu substrates were taken to examine the morphology. The structural information of the Au nanostructures from the Cu substrate, which showed a higher SERS response, was studied using selected area electron diffraction (SAED).

Fast Fourier transforms (FFTs) of various regions of the image reinforce the assignment of the fcc (111) direction of gold. Furthermore, FFTs collected separately for the particle center region and tip region were not identical, suggesting that the branched Au particles were polycrystalline in nature. High-resolution TEM shows that lattice planes extended with stacking faults or twins, indicating that they were polycrystalline. For the Au particles isolated from the Au nanostructures formed on the copper substrate, a lattice plane having an interplanar distance of 2.35 Å was measured, indicating that the growth of pods occurred preferentially on the (111) plane. The interplanar distance of 2.03 Å indicates that the crystal extends on the plane of gold. The interplanar distances 2.35 Å and 2.05 Å were calculated from the SAED and were easily indexed in JCPDS 04-0784.

In the SERS characteristics of Au nanostructures, 4-aminobenzenethiol (4-ABT) generally adsorbs strongly onto Au by forming an Au—S bond. The SERS spectra obtained from the optical experiments could be analyzed in comparison with the characteristic peaks of 4-ABT. It is noteworthy that peaks centered at 1591, 1431, 1388, 1187, 1140 and 1073 cm$^{-1}$ were much stronger than others.

Figure 12:
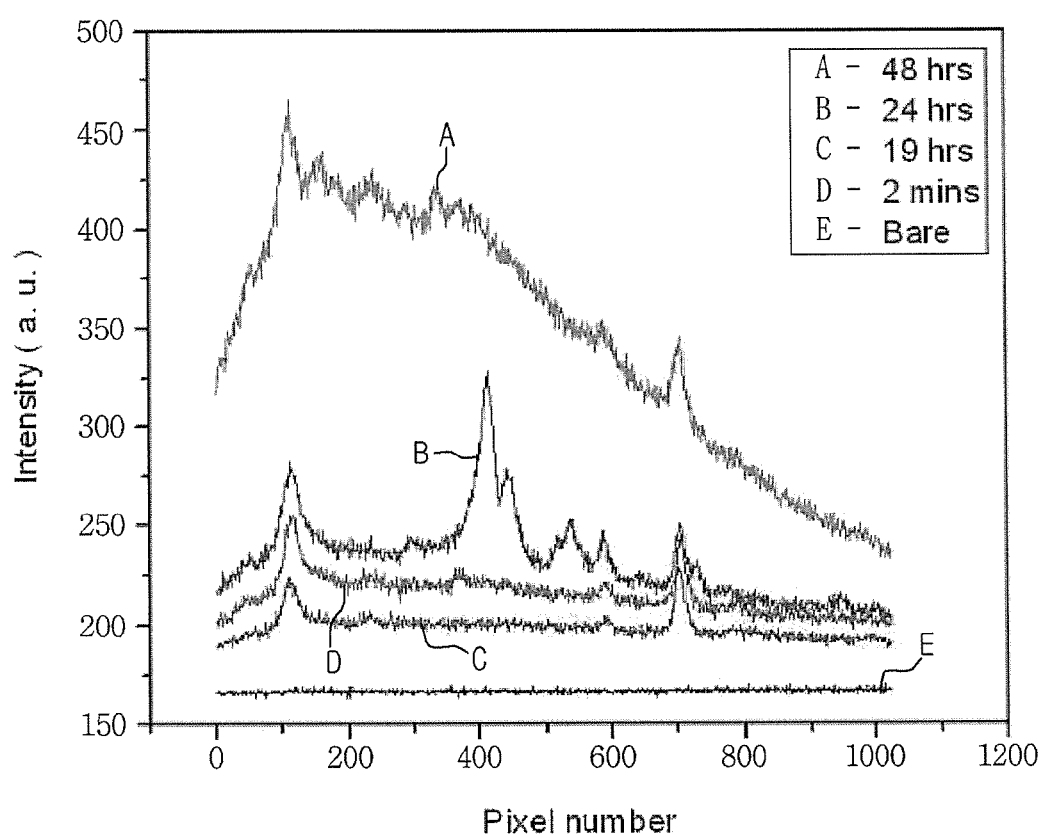
FIG. 12 shows the results of SERS analysis of Au nanostructures formed on a Pt substrate.

SERS analysis of the Au nanostructures formed on the Pt substrates was performed. FIG. 12 shows the results of the analysis. As can be seen therein, the bare Pt substrate treated with 4-ABT did not produce any SERS signal. Au nanostructures were grown for 2 min, 19 hr, 24 hr and 48 hr, and SERS signals from the Au nanostructures were measured. The sample which reacted for 24 hr produced clearly distinct peaks of 4-ABT. In the SERS spectra, more enhanced peaks were observed around 1431, 1388, 1140 and 1073 cm$^{-1}$. Here again, the Au nanostructures from the Pt substrate exhibited larger enhancement of the $b_2$ modes relative to the $a_1$ modes for the adsorbed 4-ABT molecules. The sample which reacted for 24 hr was found to be optimal for providing an excellent SERS substrate. Pt has an advantage in that it enables signal amplification to be obtained in a reaction time of 2 min or more and results in significant signal amplification, but has a disadvantage in that it is expensive.

Figure 13:
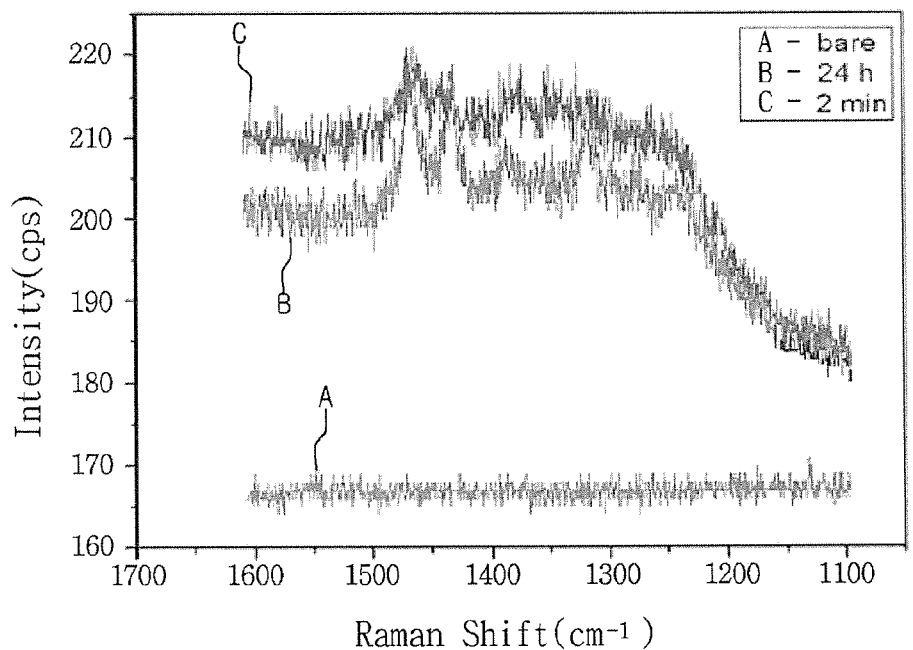
FIG. 13 shows the results of SERS analysis of Au nanostructures formed on a Cu substrate.

In addition, SERS analysis of the Au nanostructures formed on the Cu substrates was carried out. FIG. 13 shows the results of the analysis. The galvanic displacement resulted in the formation of spherical Au nanoparticles which did not exhibit any significant SERS signal. The SERS spectra obtained from the Au nanostructures on the copper substrates show that the gold nanostructures on the copper substrate exhibited an unusual larger enhancement of the $b_2$ modes relative to the $a_1$ modes for the adsorbed 4-ABT molecules. The enhancement of the $b_2$ type bands is presumably due to the chemical enhancement mechanism associated with the Au-4-ABT charge transfer. For comparison, Au was deposited on a Si substrate using e-beam evaporation. This sample was also examined for any SERS enhancement. However, there were no detectable Raman peaks on the direct e-beam Au deposited on the Si wafer. Therefore, the Au nanoflowers synthesized using this method form the SERS substrates because of the abundance of hot spots generated by their special surface topography which can result in substantial local electromagnetic field enhancement. In order to prove that the SERS spectra mainly originate from the Au nanostructures, a bare Cu substrate was analyzed for any SERS signal. It could be confirmed that there was no SERS signal from the bare substrate. SERS characterization of Au nanostructures formed on the copper substrates for different reaction times was performed. Cu has advantages over Pt in that it is inexpensive and shows similar signal amplification.

In addition, SERS characterization of the Au nanostructures on the Ag substrates was performed. The bare silver substrate holding 4-ABT molecules produced SERS enhancement. Therefore, weak SERS enhancement could be naturally observed on the bare Ag substrate. The silver substrates were allowed to react with the electroless plating solution for different reaction times of 2 min, 19 hr, 24 hr and 48 hr, and then the substrates were collected. The SERS enhancement signal from the sample collected after 2 min of the reaction was relatively stronger than those of the samples collected after 19 hr and 24 hr. This is because the Ag/Au bond present for 2 min enhances the surface Raman due to the high electromagnetic conductivity of Ag compared to Pt or Cu. For both the samples which reacted for 19 hr and 24 hr, this metal-metal bond can disappear as the Ag is replaced by Au. This suggests that Au nanoflowers are completely formed by 48 hr of the reaction, and thus SERS signal is significantly enhanced. The gold nanostructures from the silver substrate exhibited a significant SERS continuum.

Figure 14:
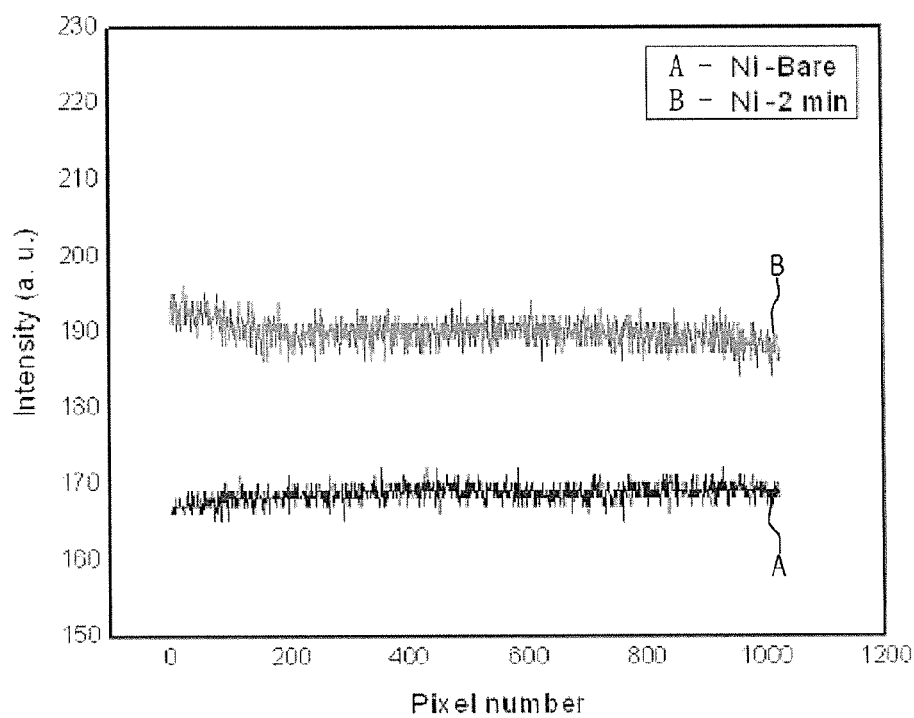
FIG. 14 shows the results of SERS analysis of Au nanostructures formed on a Ni substrate.

In addition, SERS analysis of Au structures formed on the Ni substrates. FIG. 14 shows the results of the analysis. As can be seen therein, the Au structures on the Ni substrates did not show any particular signal. Namely, only spherical structures were formed, and thus they showed signals different from those of nanoflower or nanolawn structures.

Example 4

Analysis of Factors that Influence Gold Nanostructures

Gold nanostructures are theoretically known to tend to be formed as spherical particles. This is due to nucleation energy and Gibb's free energy according to the Gibb's free energy theory, and when the nucleation energy of various structures which are formed is calculated, spherical structures are determined to have the lowest energy. Specific conditions are required for structures other than spherical structures.

1. Analysis of Influence of Temperature

Figure 7:
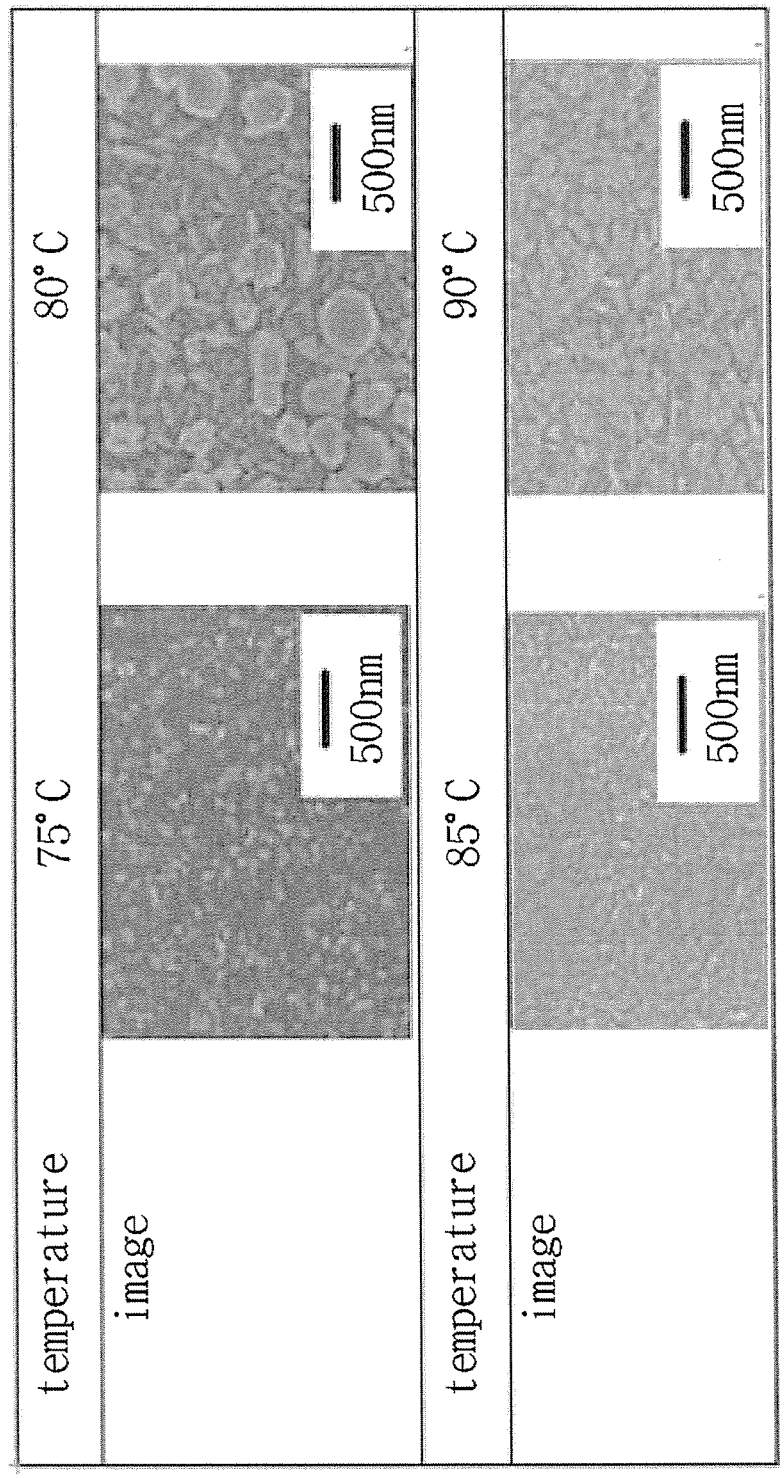
FIG. 7 shows the shape of gold nanostructures formed at different reaction temperatures.

In the present invention, the initiation temperature of the reaction was an important condition. The test was carried out at four temperatures of 75° C., 80° C., 85° C. and 90° C. At 75° C., little or no reaction occurred, and partially spherical structures were formed. At 90° C., the substrate the substrate was almost replaced by gold, and partially spherical structures together with nanoflower or nanolawn structures were formed. In the results of the reactions at 80° C. and 85° C., nanoflower or nanolawn structures could be obtained in a slightly larger amount at 85° C. FIG. 7 shows the shapes of gold nanostructures formed at various reaction temperatures.

Figure 8:
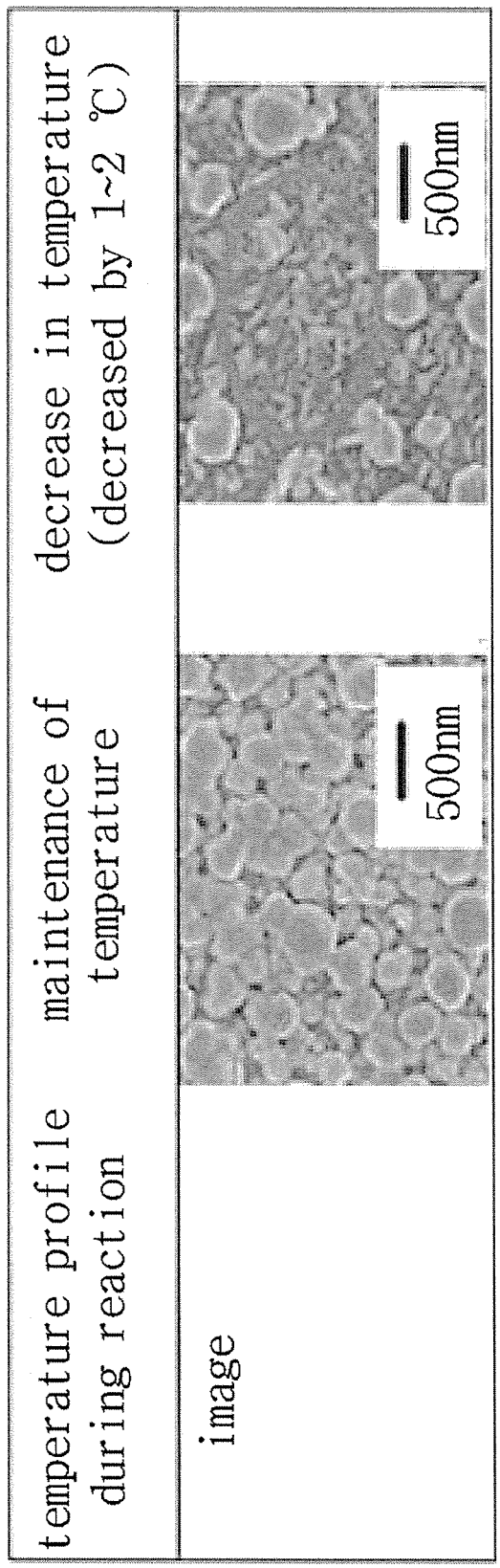
FIG. 8 shows the shapes of gold nanostructures formed while changing reaction temperature during a reaction for fabricating the gold nanostructures.

Moreover, the change in temperature during the reaction was also an important condition. It was observed that, when the initiation temperature of the reaction decreased or was maintained, significantly different structures were obtained. When the temperature was maintained, the reaction was fast, spherical structures were formed. However, when the initiation temperature of the reaction decreased during the reaction, needle-like structures were formed. The reaction rate varied depending on the temperature and had an important influence on the formation of structures. FIG. 8 shows the shape of gold nanostructures formed while changing the temperature during the reaction.

2. Analysis of Reaction Time

Figure 9:
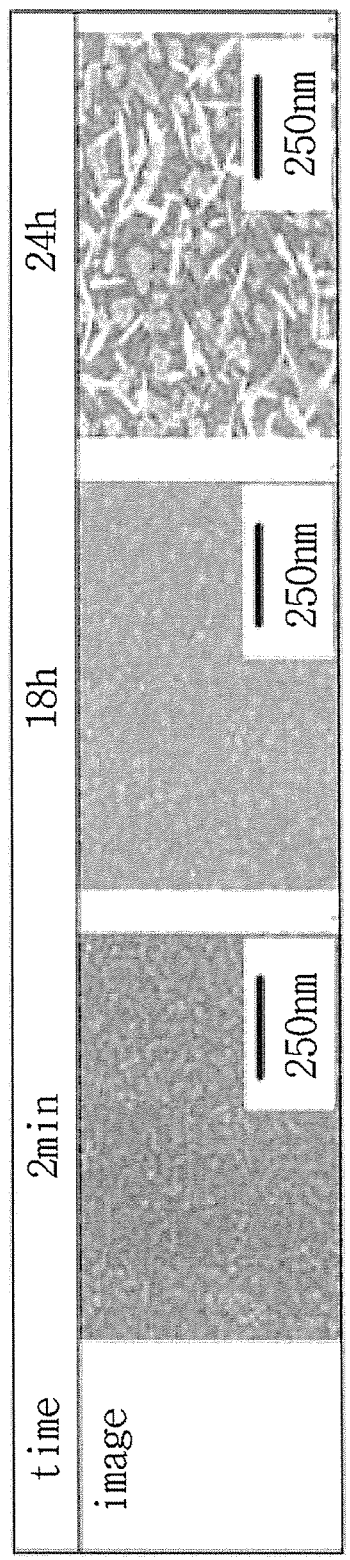
FIG. 9 shows the shapes of gold nanostructures formed for different reaction times at 80° C.

When the reaction was carried out at 80° C., needle-like structures were observed after 2 min of the reaction, and with the passage of time, spherical structures were observed, and after 24 hours, large needle-like structures were observed again. Thus, it was found that the reaction time had an influence on the formation of nanostructures. When the reaction was carried out at 85° C., it could be observed that structures identical to the structures observed after 24 hr of the reaction at 80° C. were formed after 2 min of the reaction. FIG. 9 shows the shapes of nanostructures formed for various reaction times at 80° C.

3. Analysis of Reaction Rate

Figure 10:
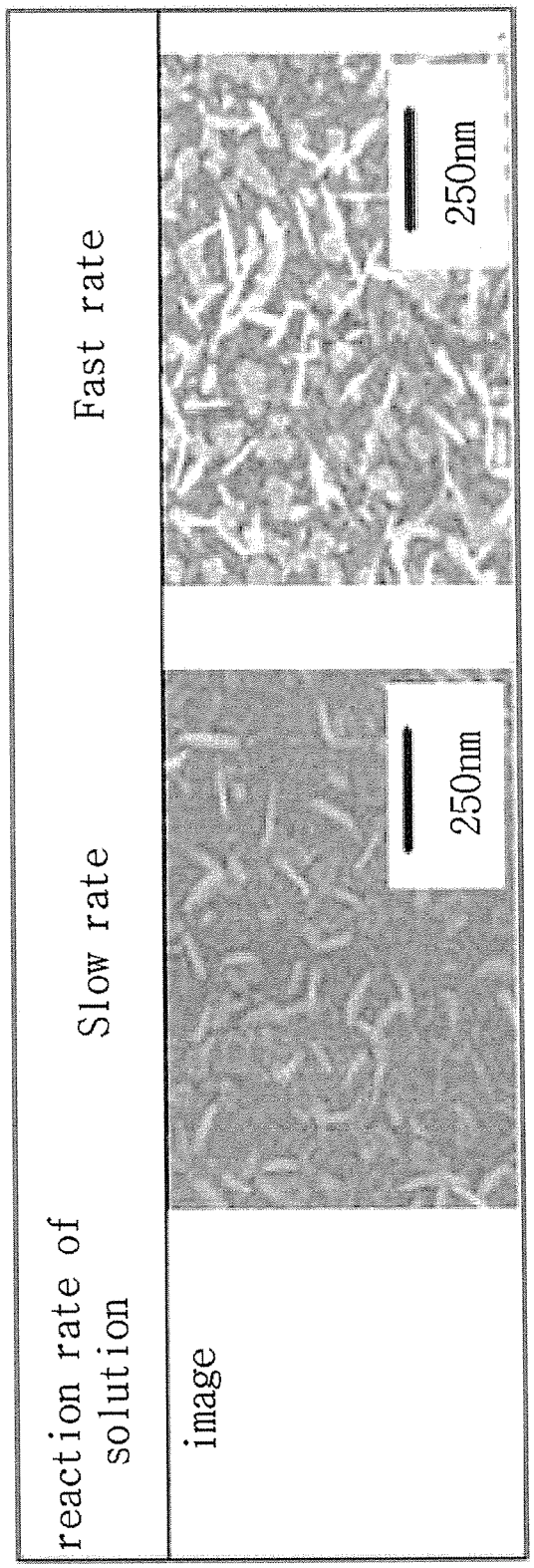
FIG. 10 shows the shapes of gold nanostructures formed at different reaction rates of a solution.

In the case of a solution having fast reaction rate, needle-like structures were observed, but these structures were relatively large, and spherical structures partially appeared. In the case of a solution having slow reaction rate, small needle-like structures could be observed, and little or no spherical structures appeared. Thus, it could be confirmed that the reaction rate had an influence on the formation of structures. FIG. 10 shows the shapes of gold nanostructures formed at various reaction rates.

4. Analysis of the Influence of Oxidation Degree of Seed Metal Layer

Figure 11:
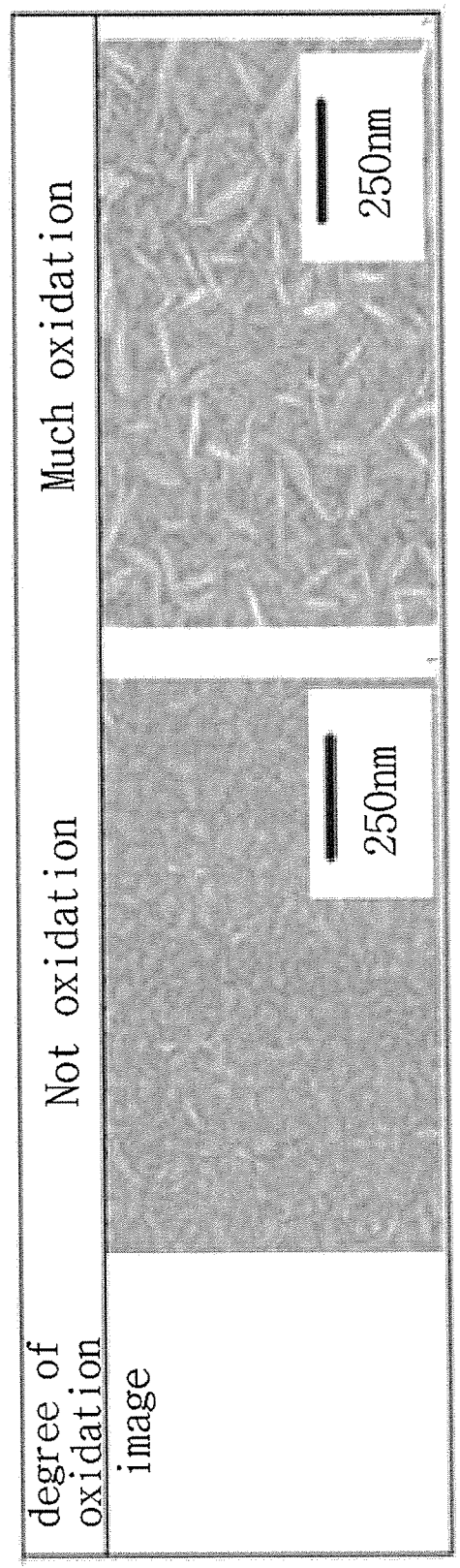
FIG. 11 shows the shapes of gold nanostructures formed using metal layers having different degrees of oxidation.

The case in which the reaction was carried out immediately after deposition of the seed metal was compared with the cases in which the reaction was carried out about 2 weeks and 4 weeks after deposition of the seed metal. After 2 minutes of the reaction, observation was performed. As a result, the largest amount of needle-like structures could be obtained in the case in which the reaction was carried out immediately after deposition of the seed metal. In addition, it could be observed that, on the oxidized surface, a relatively small amount of needle-like structures were formed. FIG. 11 shows the shapes of gold nanostructures formed using metal layers having different degrees of oxidation.

As described above, the present invention provides the simple, cost-effective and efficient method of fabricating gold nanostructures using electroless displacement plating. Surface-enhanced Raman scattering (SERS) signal or fluorescence can be measured using the gold nanostructures fabricated by the method of the present invention. In addition, the present invention enables the development of an optical sensor comprising the gold nanoparticles.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of fabricating gold nanoparticles using electroless displacement plating, the method comprising the steps of:
   depositing on a substrate a Pt, Ag or Cu metal to form a metal layer;
   reacting a gold ion-containing plating solution with the metal layer; and
   cooling the plating solution to grow the gold nanostructures on the metal layer,
   wherein the gold nanostructure is a nanoflower structure when Pt or Ag is deposited on the substrate and the gold nanostructure is a nanolawn structure when Cu is deposited on the substrate.

2. The method of claim 1, wherein the method comprises, before the depositing step, a step of depositing Ti on the substrate.

3. The method of claim 1, wherein the reacting step is carried out at a temperature of 80~90° C. while initiation temperature of the reaction is decreased by 1~5° C. during the reaction.

4. The method of claim 1, wherein the reacting step is carried out for 2 minutes or more.

5. The method of claim 1, wherein the reacting step is carried out by stirring the plating solution at a rate of 10-100 rpm.

6. The method of claim 1, wherein the reacting step is carried out before oxidation of the metal occurs after deposition of the metal layer.

7. The method of claim 1, wherein the method further comprises a step of coating the fabricated gold nanostructures with a positively charged polymer.

8. The method of claim 7, wherein the positively charged polymer is selected from the group consisting of polyethylene imine or its derivatives, polylysine, chitosan, poly-aspartic acid, spermine, protamine, polyamidoamine, polypropyleneimine, polybrene, polyacrylamide, polyvinyl amine, and DEAE-dextran.

9. A method of measuring surface-enhanced Raman scattering (SERS) signal or fluorescence using gold nanostructures fabricated according to the method of claim 1.

10. The method of claim 9, wherein a fluorescent molecule having a quantum yield of less than 50% is used.

11. The method of claim 10, wherein the fluorescent molecule is Cy3.

* * * * *